| United States Patent [19] | [11] | 4,356,070 |
|---|---|---|
| Baucom | [45] | Oct. 26, 1982 |

[54] METHOD FOR SYNTHESIZING POLY(CARBONYL FLUORIDE) OLIGOMERS

[75] Inventor: Keith B. Baucom, Gainesville, Fla.

[73] Assignee: The United States of America as represented by the Secretary of the Air Force, Washington, D.C.

[21] Appl. No.: 274,574

[22] Filed: Jun. 17, 1981

[51] Int. Cl.³ ............................................. B01J 19/12
[52] U.S. Cl. ................................................ 204/158 R
[58] Field of Search .................................... 204/158 R

[56] References Cited

U.S. PATENT DOCUMENTS

| 2,575,125 | 11/1951 | Prober | 260/82.1 |
|---|---|---|---|
| 2,700,661 | 1/1955 | Miller | 260/87.5 |
| 3,442,942 | 5/1969 | Sianesi et al. | 204/158 R |
| 3,706,773 | 12/1972 | Anello et al. | 260/408 |
| 3,896,167 | 7/1975 | Sianesi et al. | 260/544 F |
| 4,003,941 | 1/1977 | Crawford et al. | 260/463 |

*Primary Examiner*—Howard S. Williams
*Attorney, Agent, or Firm*—Donald J. Singer; William J. O'Brien

[57] ABSTRACT

F-3-Methylbutene-1 has been oxidized using oxygen and ultraviolet radiation to form poly(carbonyl fluoride) oligomers. The formation of fluoroformate terminated material is insignificant. This is in sharp contrast to the products derived from the prior art oxidation of F-propene (HFP) in which up to 60% fluoroformate terminated material was produced. F-Ethylene (TFE) can be added to the F-3-methylbutene-1 reaction gas stream without adversely affecting the product composition. The fluoride oligomers, after addition of one unit of hexafluoropropylene oxide, can be converted to s-triazines which have excellent properties as hydrualic fluids.

4 Claims, No Drawings

METHOD FOR SYNTHESIZING POLY(CARBONYL FLUORIDE) OLIGOMERS

STATEMENT OF GOVERNMENT INTEREST

The invention described herein may be manufactured and used by or for the Government for governmental purposes without the payment of any royalty thereon.

BACKGROUND OF THE INVENTION

This invention relates to poly(carbonyl fluoride) oligomers. In a more particular aspect, this invention concerns itself with an improved method of synthesizing poly(carbonyl fluoride) oligomer acid fluorides, which can be converted to s-Triazines having perfluorinated polyether substituents of the type illustrated by the following general formula

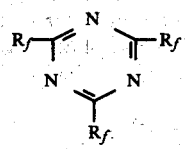

where $R_f = CFXCF_2O(CFXCF_2O)_n CFX$ and $X = CF_3$ or $F$.

The s-triazines have been found to be particularly useful as candidates for high temperature fluids which in turn serve as base stocks for advanced hydraulic fluids, coolants, gas turbine engine oils and greases. These fluids possess desirable properties such as inherent stability at temperatures up to 700° F., excellent compatibility with metals up to 650° F., good lubricity and nonflammability. These characteristics make them excellent candidates for a wide temperature range, nonflammable, hydraulic fluid. However, their low temperature rheological properties and moderately high volatility have been their only deficiencies. These deficiencies, however, can be improved by increasing their oxygen to carbon, (O/C) ratio. This increase in O/C ratio has been accomplished by the use of poly(carbonyl fluoride) oligomers. However, the principal short-coming of this system has been the low yield of selected oligomers and their low molecular weight.

In an attempt to overcome the problems associated with previous methods of preparing poly(carbonyl fluoride) oligomers, it was found that the photoxidation of F-3-methylbutene-1 in the presence of ultraviolet radiation using a low pressure mercury lamp produced the desired oligomers with only an insignificant amount of fluoroformate terminated material being produced as a reaction by-product. In previously used methods of synthesis, fluoroformate terminated material was produced in significant amounts and had to be removed before the oligomers could be utilized in the synthesis of forming desired s-triazine high temperature fluids.

SUMMARY OF THE INVENTION

In accordance with this invention, a novel route for the synthesis of poly(carbonyl fluoride) oligomers has been found. The synthesis is accomplished by oxidizing F-3-methylbutene-1 using oxygen and ultraviolet radiation. The formation of fluoroformate terminated material is insignificant. This is in sharp contrast to the products derived from the oxidation of F-propene during which up to 60% fluoroformate terminated material is formed. Tetrafluoroethylene (TFE), also known as F-ethylene, can be added, if desired, to the F-3-methylbutene-1 gas stream without adversely affecting the product composition. In fact, addition of TFE reduces the cost of the product and increases the yield. These materials after addition of one unit of hexafluoropropylene oxide can be converted to s-triazines which have excellent properties as hydraulic fluids.

Accordingly, the primary object of this invention is to provide a simple and efficient route for the synthesis of poly(carbonyl fluoride) oligomers.

Another object of this invention is to provide a novel method for synthesizing poly(carbonyl fluoride) oligomers in which the formation of fluoroformate terminated material is insignificant.

Still another object of this invention is to provide a novel method of preparing poly(carbonyl fluoride) oligomers through the photooxidation of F-3-methylbutene-1.

The above and still other objects and advantages of the present invention will become more readily apparent after consideration of the following detailed description thereof.

DESCRIPTION OF THE PREFERRED EMBODIMENTS

With the above-defined objects in mind, the present invention involves a novel method for preparing poly(carbonyl fluoride) oligomers which find particular utility as a reaction component in the synthesis of s-triazine based hydraulic fluids. The s-triazines which have perfluorinated polyether substituents have been found to be particularly adaptable in the synthesis of thermally and oxidatively stable fluids with a wide variation in fluid properties. These materials have the following general structure

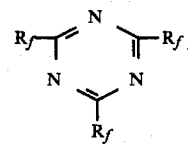

where $R_f = CFXCF_2O(CFXCF_2O)_n$ CFX— and $X = CF_3$ or $F$.

Perfluoroalkylene oxide s-triazines, for example, have been used successfully as hydraulic fluids. These triazines are essentially of two types—those having substituents derived from hexafluoropropene oxide (HFPO) where $X = CF_3$ and those with substituents derived from tetrafluoroethylene oxide (TFEO) where $X = F$.

In general, HFPO-derived mono-triazines have good viscosity characteristics but relatively high pour points. The opposite is true with TFEO-derived triazines, which have adequately low pour points but too low viscosities.

An important finding of the experimental work associated with these materials is that the low temperature properties of perfluoroalkylene oxide s-triazines are directly related to the carbon-oxide ratio of the triazine molecule. For a given molecular weight, the lower the C/O ratio the lower is the pour point of the fluid.

It becomes obvious, therefore, that any further improvement in the rheological properties of the triazines requires a lower C/O ratio. This has been accomplished heretofore by the preparation of carbonyl fluoride oligomers of the type illustrated by structure II in the following equations; and the resulting synthesis of the corresponding triazines.

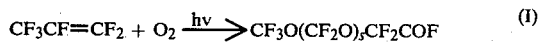

$$CF_3CF{=}CF_2 + O_2 \xrightarrow{h\nu} CF_3O(CF_2O)_xCF_2COF \quad (I)$$

$$CF_3O(CF_2O)_xCF_2COF \xrightarrow{HFPO} \quad (II)$$

$$CF_3O(CF_2O)_xCF_2CF_2{-}O[CF(CF_3)CF_2O]_{n-1}CF{-}(CF_3)COF$$

The accumulated data on HFPO-terminated carbonyl fluoride triazines derived from oligomers of structure II indicates that the incorporation of a relatively small amount of the carbonyl fluoride oligomer greatly improves the low temperature properties of the triazine fluid.

The major drawbacks in the preparation of a triazine of this nature, however, are the low yields obtained in the preparation of the polycarbonyl fluoride oligomer acid fluorides and the experimental difficulties in adding more than one HFPO capping group. As a result, a major research effort has evolved in an attempt at finding more economical ways of preparing polycarbonyl fluoride oligomer acid fluorides used in the preparation of triazine fluids and in finding more economical preparative routes to the synthesis of polycarbonyl fluoride acid fluorides.

As a result of this research effort, it was found that poly(carbonyl fluoride) oligomers could be prepared through the photooxidation of F-3-methylbutene-1 using oxygen and ultraviolet radiation. A low pressure mercury vapor lamp was utilized to provide the oxidation for the gas phase reaction.

The mechanism postulated for the oxidation of the F-3-methylbutene-1 is given below

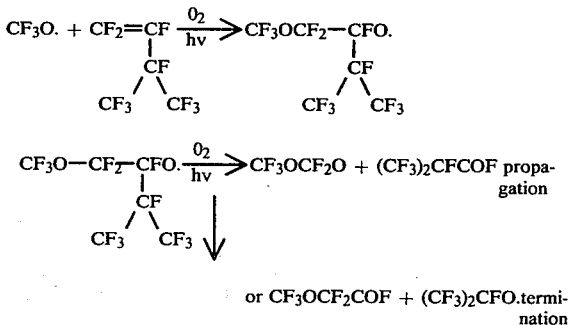

One molecule of F-isobutyryl fluoride is formed for each CF$_2$O unit incorporated in the growing chain. One molecule of F-acetyl fluoride is formed when a radical chain is terminated.

The static gas phase photooxidation of F-3-methylbutene-1 provides a series of higher molecular weight poly(carbonyl fluoride) oligomer acid fluorides without any evidence of fluoroformate formation. Attack of the —CF$_2$O has occurred exclusively on the CF$_2$ carbon of the olefin. The fluoroformate problem, which occurred with previously known methods of synthesis, has been solved.

Yields of hydraulic fluids are now much higher because all of the oligomer material can be used. Under static conditions, the prior art hexafluoropropene method (HFP) gave 7.2% yield of poly(carbonyl fluoride) oligomer acid fluorides while the butene oxidation method of this invention provides a 46% yield. The introduction of tetrafluoroethylene (TFE) does not increase the yield of higher molecular weight acid fluorides produced through the oxidation of HFP, but the addition of TFE to the present method did increase the yield of product.

A fog was observed within the reaction flask as the oxidation proceeded when the reaction progressed to give the desired acid fluorides. When this phenomenon was not observed no oxidation took place and starting materials were recovered. Ultra violet radiation was required in the oxidation since no oxidation was observed during a 24-hour period when the reaction was attempted using a sun lamp as the light source. A 1-liter resin kettle was employed to carry out the large scale gas phase photooxidation of F-3-methylbutene-1. Several small runs using in each ca. 15 g of F-3-methylbutene-1 were carried out varying the oxygen ratio, addition rate of olefin, and reaction temperature to establish the most favorable conditions for the preparation of poly(carbonyl fluoride) oligomeric acid fluorides. The light source for all of the photooxidations was a low pressure mercury arc lamp having an output of 2.5 watts at 2537 A.

1200 g of F-3-methylbutene-1, which had been prepared, was oxidized over a three-week period to give 130 g of usable acid fluoride product. The gas phase photooxidation was found to be an order of magnitude slower than HFP oxidation and similar to the rate of oxidation of TFE. The desired higher molecular weight poly(carbonyl fluoride) oligomers were obtained from the oxidation.

The following examples are presented to show the photooxidation of F-3-methylbutene-1 and to further illustrate the nature of the invention and how it may be carried into effect. Although the examples depict specific embodiments of the invention, they are not to be construed as limiting the scope of the invention in any way.

EXAMPLE I

A one-liter, one necked flask was equipped with a magnetic stirring bar and a stopcock adapter for introducing the starting materials. After the flask had been evacuated to full vacuum, the F-3-methylbutene-1 (300 mm pressure; 97% pure) and oxygen (300 mm pressure) were added and a commercial 275-watt sunlamp was used to irradiate the stirred mixture. After irradiation for 24 hours, a pink vapor in the flask and small iodine crystals growing from the side of the reaction vessel were observed. An infrared spectrum showed unreacted F-3-methylbutene-1 and several small unidentified impurities. This reaction was repeated using 99+% pure F-3-methylbutene-1 with no reaction occurring during a 24 hour period.

EXAMPLE II

Using the same one-liter flask as in Example I, and an adaptor to include a low pressure mercury uv lamp for internal irradiation, the reaction was repeated. The flask was evacuated and 300 mm each of F-3-methylbutene-1 and oxygen were admitted. As soon as the lamp was turned on, a mist was observed in the neck of the flask and the pressure decreased at an average rate of 5 mm/min for 30 min and then ceased to decrease. The lamp was turned off and the flask was immersed in liquid oxygen. The total pressure of non-condensable material was 30 mm. The flask was warmed to ambient temperature and the volatile material was transferred to a Fisher-Porter ampoule. Infrared spectra were taken of the gaseous product and of the liquid residue which did not transfer. No carbonyl fluoride was observed in the overgas (IR) and a GLC analysis indicated the gaseous product to be 80% one component [expected $(CF_3)_2CFCOF$]. The GLC analysis was carried out on a 5710A Hewlett Packard model GLC, using a 3% WF-1 column 6'×⅛", packed with 100/120 mesh acid washed Chromosorb Q. The injection port was at 150° C. with the detector at 250° C. and a carrier gas flow rate of 20 cc/min.

The infrared spectrum showed no unreacted starting material and showed that an acid fluoride was the major constituent. The liquid sample also contained acid fluorides (IR). GLC showed it to be an oligomeric series.

EXAMPLE III

A 1-liter, one-necked flask was equipped with a magnetic stirring bar, a low pressure mercury uv lamp and a stopcock adapter for introducing starting materials. The system was evacuated and 500 mm of oxygen was admitted to the flask. With the uv lamp on, F-3-methylbutene-1 was added in 150 mm increments until 450 mm had been added. Following each addition the pressure decreased as the monomer was consumed. Then 300 mm of $O_2$ was again introduced and the remaining 150 mm of olefin was added. After the decrease in pressure had become negligible, an infrared spectrum of the gas phase was taken. It showed some unreacted starting material. A GLC of the gaseous product indicated 80% completion of the oxidation with the predominant product being $(CF_3)_2CFCOF$.

EXAMPLE IV

The reaction of Example III was repeated using 800 mm of each reagent. The gaseous products showed (IR) no unreacted starting material. Using static vacuum transfer to a −183° C. trap, the volatile material was collected. A pressure of 100 mm Hg remained in the system following this transfer. Methanol (10 cc) was added to the reaction vessel and the product was collected. The excess methanol was removed by extraction with water. The organic layer was collected and dried over molecular sieves. An infrared spectrum of the product showed a methyl ester carbonyl absorption as well as C–F stretch absorptions. A GLC of this ester fraction showed what was believed to be $(CF_3)_2CFCO_2CH_3$ as the predominant product with the remainder being an oligomeric series.

EXAMPLE V

To obtain a larger amount of oxidation products from F-3-methylbutene-1, a large scale reaction was run in a 3-liter flask. There was 12 g of olefin used and the oxidation was carried out with a low pressure uv lamp. The reaction was monitored by infrared and worked up by adding 100 cc of methanol to the reaction flask followed by a water wash of the methanol solution with 600 cc of deionized water. The lower organic layer was separated, and dried over molecular sieves. GLC showed a low boiling component (ca. 10%), a major fraction (67%) and an oligomeric mixture. The product was distilled to give 1.1 g of fraction 1 identified as methyl trifluoroacetate and 5.5 g of fraction 3 identified as methyl perfluoroisobutyrate. This confirms the original proposed mechanism for this reaction.

EXAMPLE VI

A control reaction was carried out on a new batch of F-3-methylbutene-1 in which 300 mm was oxidized in a one-liter, one-necked flask as in previous reactions. The products were isolated by adding 10 cc of methanol followed by a water wash with 100 cc. The products were separated, dried over molecular sieves and a GLC indicated the same ratio of products as in previous oxidations.

EXAMPLE VII

A large scale oxidation of F-3-methylbutene-1 was carried out in a one-liter reactor equipped with a low pressure u.v. lamp and gas inlets for the gases. A total of 127 g of F-3-methylbutene-1 was oxidized over a 26 hour period. The products were collected as the methyl esters and 11 g of higher molecular weight poly(carbonyl fluoride) oligomer esters were collected.

700 g of F-3-methylbutene-1 were oxidized after drying the starting olefin over molecular seives. The oxidation was accomplished over a 200 hour period. The higher molecular weight products were combined and found to be the acids of poly(carbonyl fluoride) oligomers. The yield was 130 g or 18.6% weight yield. A theory of 26.4% weight yield represents 100% yield, therefore a 70% yield was realized.

Two reactions were carried out oxidizing F-3-methylbutene-1 with tetrafluoroethylene in the vapor phase. A 100-ml reactor was equipped with a low pressure u.v. lamp and gas inlets for oxygen, F-3-methylbutene-1 and tetrafluoroethylene. After 11 hours, 37 g of F-3-methylbutene-1 had been oxidized along with 11 g of tetrafluoroethylene. The products were collected as the methyl esters (3.6 g of material bp 100° C.).

The oxidation of F-3-methylbutene-1 and tetrafluoroethylene was also carried out in a three-liter resin kettle equipped with a low pressure uv lamp, gas inlet tubes for the introduction of the monomers, and a gas outlet to the ice water and dry ice/acetone cooled traps. The reactor was cooled to 0° C. as the lamp was turned on and the oxygen was admitted. The F-3-methylbutene-1 addition was started at 0.005 moles/hour and the oxygen flow at a rate of 0.1 moles/hour. After 30 minutes, the tetrafluoroethylene addition was begun at 0.003 moles/hour was run and the reaction was on for 192 hours to oxidize 495 g of F-3-methylbutene-1. The products were collected and found to be the acids derived from the poly(carbonylfluoride) oligomers.

While the invention has been described with particularity in reference to specific embodiments thereof, it is to be understood that the disclosure of the present invention is for the purposes of illustration only and is not intended to limit the invention in any way, the scope of which is defined by the appended claims.

I claim:

1. A method for preparing poly(carbonyl fluoride) oligomers comprising the steps of:
    A. subjecting a mixture of F-3-methylbutene-1 and gaseous oxygen to a source of ultraviolet radiation for a period of time sufficient to effect a photolytic reaction between the components of said mixture; and
    B. separating the resulting reaction products.

2. A method in accordance with claim 1 wherein the concentration of oxygen is greater than or equal to the total concentration of F-3-methylbutene-1.

3. A method in accordance with claim 1 wherein said ultraviolet radiation is induced by a low pressure mercury arc lamp.

4. A method in accordance with claim 1 and further including the addition of tetrafluoroethylene to said reaction mixture.

* * * * *